US010905398B2

(12) United States Patent
Bruestle et al.

(10) Patent No.: US 10,905,398 B2
(45) Date of Patent: Feb. 2, 2021

(54) ULTRASOUND TRANSDUCER ARRAY WITH SEPARATED ACOUSTIC AND ELECTRIC MODULE

(71) Applicant: General Electric Company, Schenectady, NY (US)

(72) Inventors: Reinhold Bruestle, Frankenburg am Hausruck (AT); David A. Chartrand, Mesa, AZ (US); Thomas Rittenschober, Nussdorf am Attersee (AT); Scott William Easterbrook, Bainbridge Island, WA (US); Manuel Schoenauer, Thalgau (AT); Andreas Kremsl, Wolfgang im Salzkammergut (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1029 days.

(21) Appl. No.: 14/986,913

(22) Filed: Jan. 4, 2016

(65) Prior Publication Data

US 2017/0188995 A1   Jul. 6, 2017

(51) Int. Cl.
*A61B 8/00* (2006.01)

(52) U.S. Cl.
CPC .......... *A61B 8/4483* (2013.01); *A61B 8/4427* (2013.01)

(58) Field of Classification Search
CPC ... A61B 8/4483; A61B 8/4427; A61B 8/4494; A61B 8/4444
See application file for complete search history.

(56) References Cited

U.S. PATENT DOCUMENTS

| 5,961,465 A * | 10/1999 | Kelly, Jr. ............... A61B 8/546 |
| | | 600/459 |
| 7,892,176 B2 | 2/2011 | Inodnicki et al. |
| 8,742,646 B2 | 6/2014 | Wodnicki et al. |
| 9,072,487 B2 | 7/2015 | Hebrard et al. |
| 2008/0273424 A1* | 11/2008 | Wodnicki ............. A61B 8/0833 |
| | | 367/180 |
| 2009/0034370 A1* | 2/2009 | Guo ..................... B06B 1/0622 |
| | | 367/180 |
| 2012/0267981 A1 | 10/2012 | Morris et al. |

(Continued)

FOREIGN PATENT DOCUMENTS

| WO | 2015099836 A1 | 7/2015 |
| WO | 2015102673 A1 | 7/2015 |

*Primary Examiner* — Bill Thomson
*Assistant Examiner* — Aminah Asghar
(74) *Attorney, Agent, or Firm* — McCoy Russell LLP

(57) ABSTRACT

Systems are provided for the arrangement of decoupled electric and acoustic modules for a transducer array of an ultrasound probe. In one embodiment, the decoupled modules are independently coupled to a flex interconnect, apart from one another, allowing for electric communication between all modules through the flex interconnect. As one example, an ultrasound transducer array for an ultrasound probe comprises an acoustic backing, a flex interconnect coupled to the backing at a first surface of the flex interconnect, a matrix acoustic array coupled to a second surface of the flex interconnect, the second surface opposite the first surface, and an electric module coupled to the second surface of the flex interconnect at a location spaced away from where the matrix acoustic array is coupled to the flex interconnect.

10 Claims, 6 Drawing Sheets

(56) References Cited

U.S. PATENT DOCUMENTS

| | | | |
|---|---|---|---|
| 2013/0188446 A1* | 7/2013 | Kubota | B06B 1/0622 367/7 |
| 2013/0190627 A1* | 7/2013 | Jun | A61B 8/4494 600/472 |
| 2013/0315035 A1* | 11/2013 | Tai | B06B 1/0622 367/140 |
| 2013/0336551 A1* | 12/2013 | Clingman | A61B 5/0095 382/128 |
| 2014/0088431 A1* | 3/2014 | Miyazawa | B06B 1/207 600/459 |
| 2014/0116139 A1* | 5/2014 | Endo | B06B 1/0622 73/584 |
| 2015/0087988 A1 | 3/2015 | Lee et al. | |
| 2015/0099978 A1* | 4/2015 | Davidsen | A61B 8/546 600/459 |
| 2015/0182194 A1 | 7/2015 | Bruestle et al. | |
| 2017/0164926 A1* | 6/2017 | Spicci | A61B 8/4281 |
| 2018/0125461 A1* | 5/2018 | Clark | A61B 8/4444 |

* cited by examiner

ULTRASOUND TRANSDUCER ARRAY WITH SEPARATED ACOUSTIC AND ELECTRIC MODULE

FIELD

Embodiments of the subject matter disclosed herein relate to ultrasound transducers, and more particularly, to a system and method for assembling an ultrasound transducer array using acoustic and electric modules.

BACKGROUND

Ultrasound transducers are used extensively for ultrasound imaging of an object. Particularly, in a medical field, the ultrasound transducers are typically used to obtain a high quality image of a region within a patient. Further, this high quality image may be used for diagnosing the patient.

An ultrasound transducer typically includes transducer arrays that are generally used for transmission and reception of ultrasonic or acoustic waves. These acoustic waves are further processed to obtain the image of the object. In general, the transducer arrays may be flat transducer arrays or convex transducer arrays. The flat transducer arrays are commonly used in cardiac imaging while, the convex transducer arrays are used in other diagnostic applications, such as abdominal imaging.

Typically, the transducer arrays are in direct contact with beam forming electronics or an application specific integrated circuit (ASIC). For example, the array may include multiple acoustic modules, each including a plurality of acoustic elements, and multiple ASICs. In one embodiment, one of the acoustic modules and electric modules (e.g., ASICs) may be combined into a stacked and integrated module. However, in this configuration it may be difficult to form curved arrays without damaging the ASICs, and the ASIC pitch and array pitch must match. Further, both the ASIC and the acoustic elements of the acoustic module may produce a significant amount of heat during use. Thus, coupling these heat sources together may further increase heat output of the ultrasound transducer, thereby increasing the heat transfer requirements of the ultrasound transducer.

BRIEF DESCRIPTION

In one embodiment, an ultrasound transducer array for an ultrasound probe comprises an acoustic backing, a flex interconnect coupled to the backing at a first surface of the flex interconnect, a matrix acoustic array coupled to a second surface of the flex interconnect, the second surface opposite the first surface, and an electric module coupled to the second surface of the flex interconnect at a location spaced away from where the matrix acoustic array is coupled to the flex interconnect. By utilizing a flex interconnect the matrix acoustic array (e.g., acoustic module) may be decoupled (e.g., spaced apart) from the electric module, while still preserving electrical connections between the matrix acoustic array and electric module. In this way, the matrix acoustic array and electric module of the transducer array may assume a plurality of geometric configurations without damage to the electric module (which may include ASICs). Additionally, decoupling of the matrix acoustic array and electric module allows these components to have separate pitches, as well as separate heat sinks, thereby decreasing constraints on ultrasound probe manufacturing and increasing probe functionality (e.g., by increasing the possible geometric configurations of modules within the probe, and by increasing the amount of energy that may be transmitted into a patient's anatomy by the ultrasound probe, for enhanced image quality, while still satisfying surface temperature regulations).

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
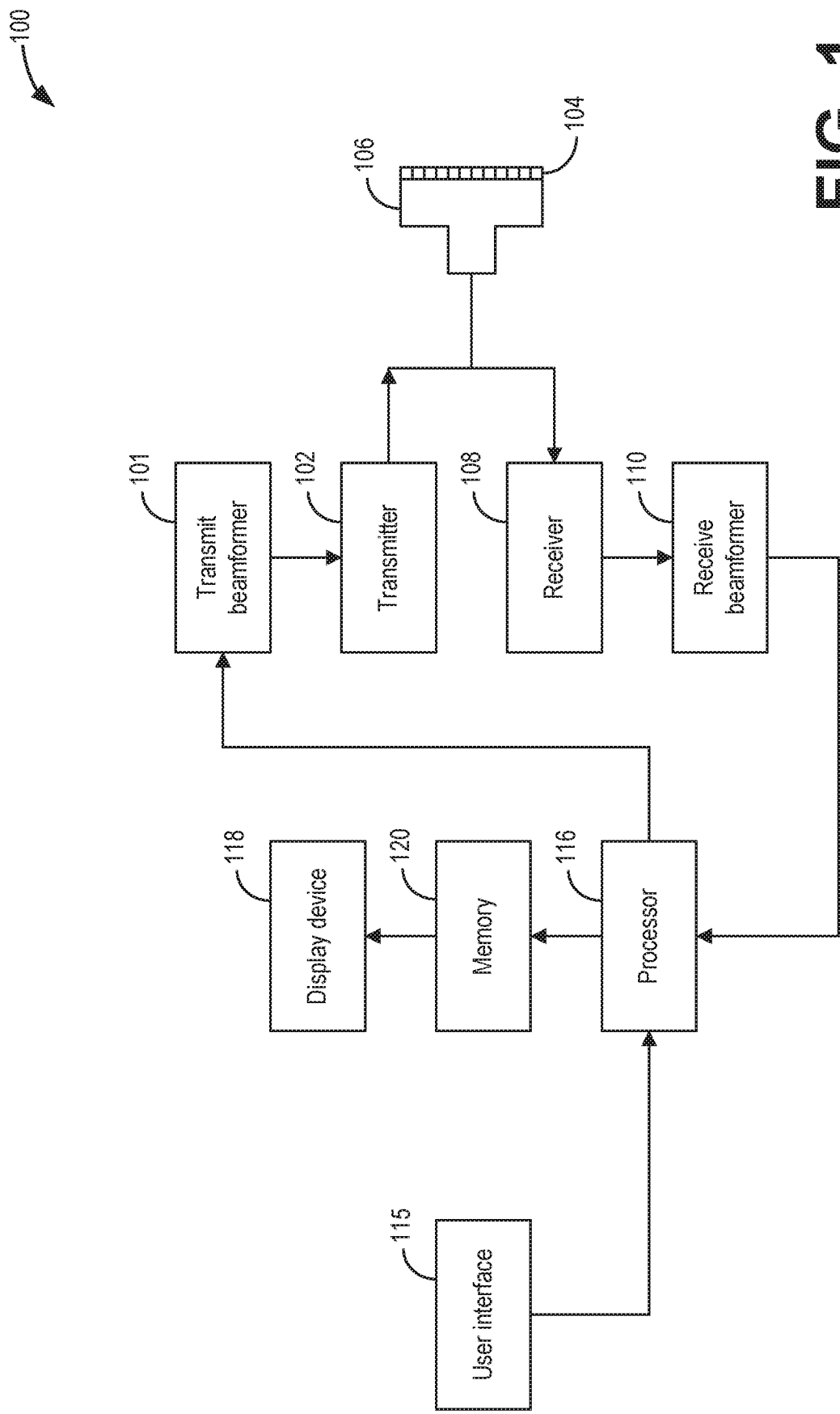
FIG. 1 shows an ultrasonic imaging system according to an embodiment of the invention.
Figure 2:
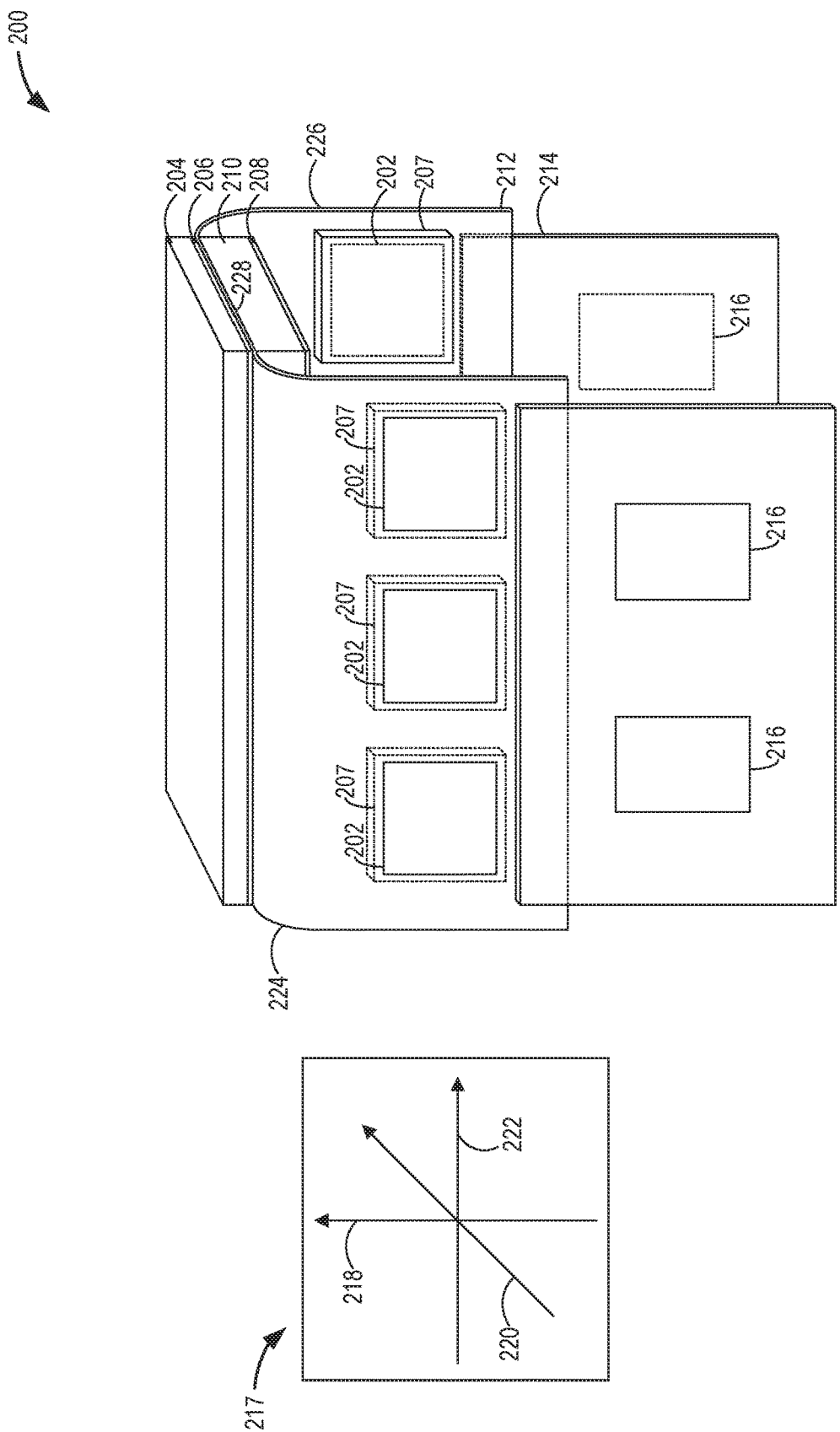
FIG. 2 shows a perspective view of a linear transducer array having electric and acoustic modules, according to an embodiment of the invention.
Figure 3:
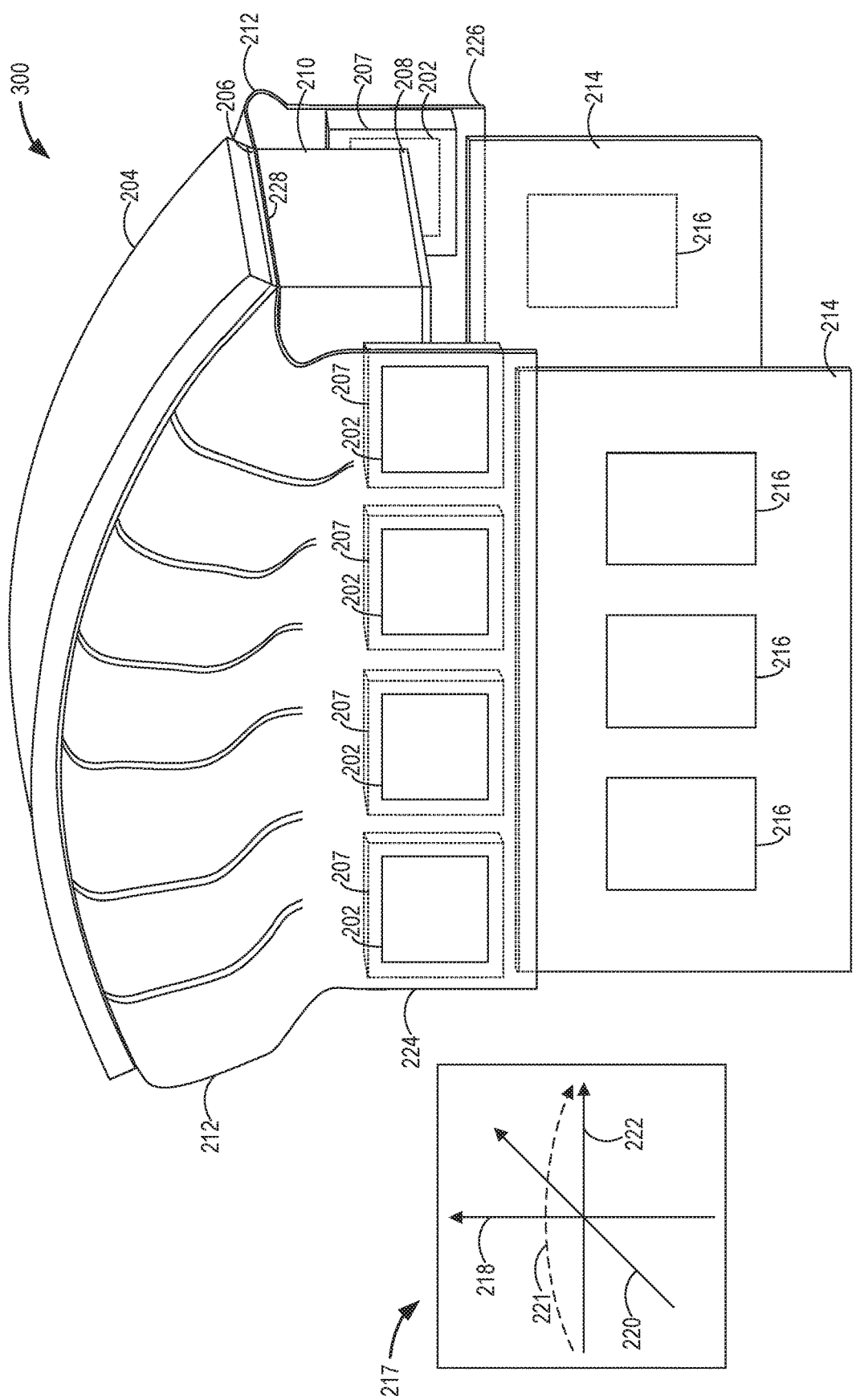
FIG. 3 shows a perspective view of a curved transducer array having electric and acoustic modules, according to an embodiment of the invention.
Figure 4:
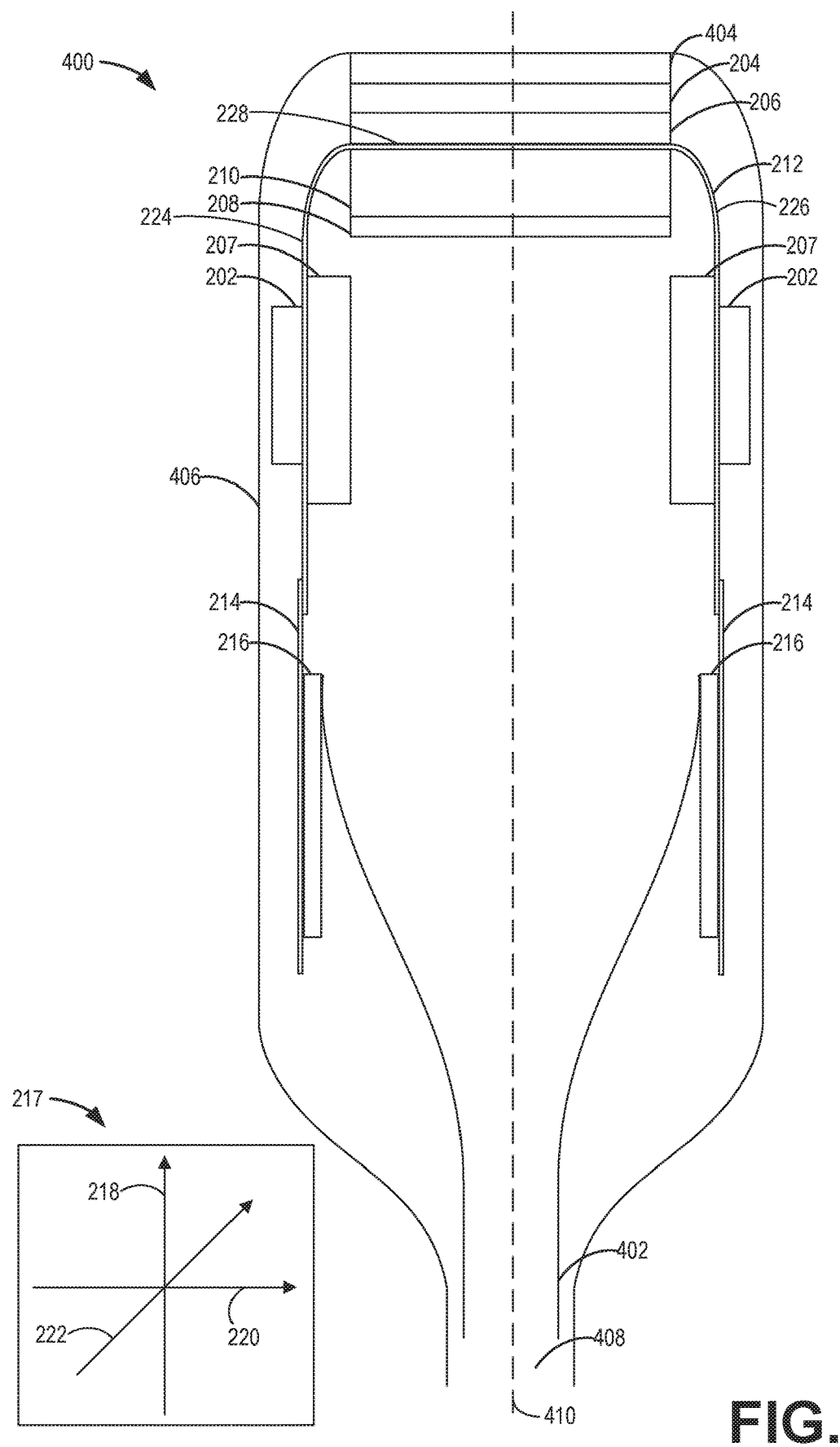
FIG. 4 shows a cross-sectional side view of an embodiment of an ultrasound probe, in accordance with aspects of the present disclosure.
Figure 5:
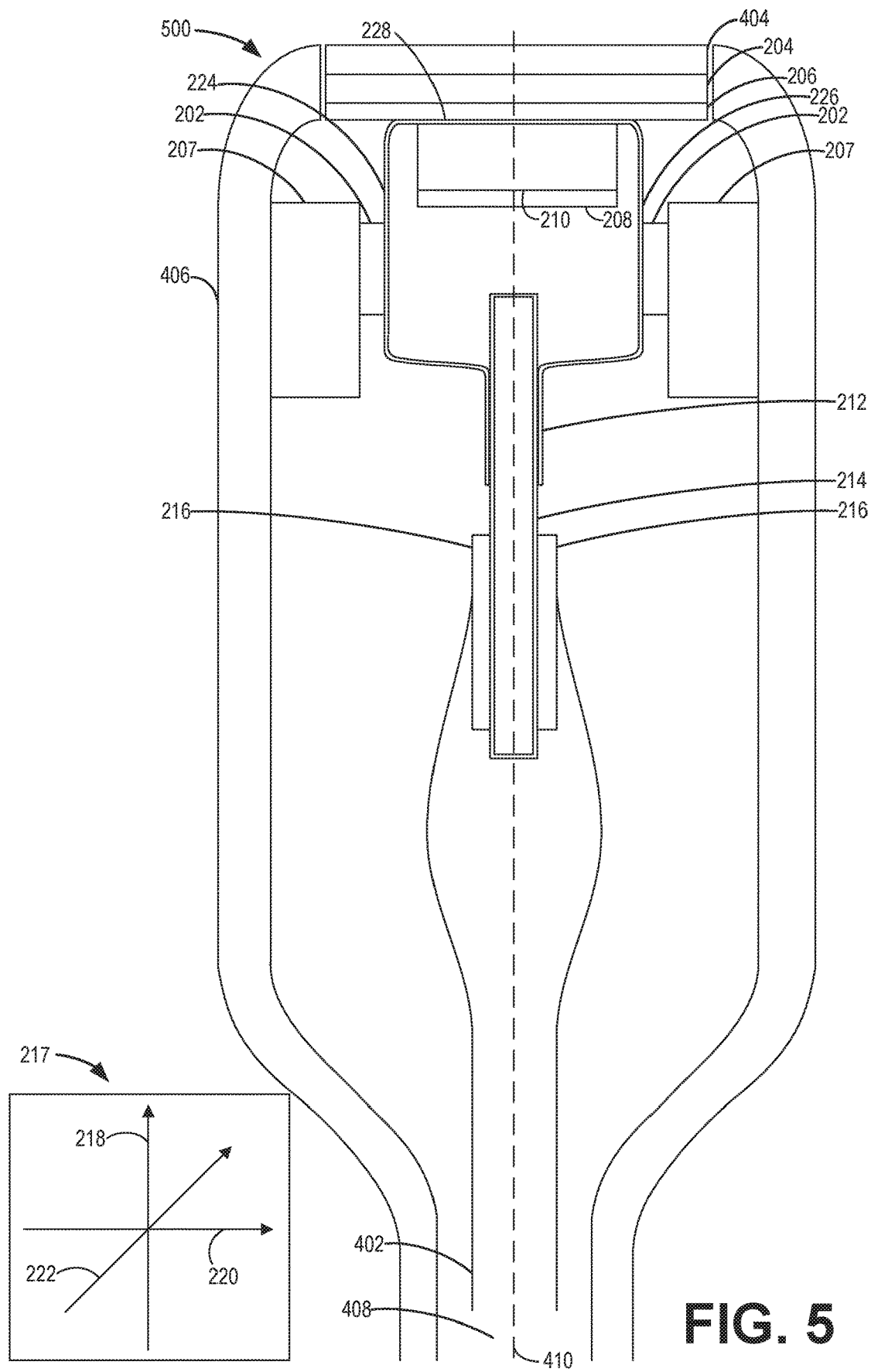
FIG. 5 shows a cross-sectional side view of a second embodiment of an ultrasound probe, in accordance with aspects of the present disclosure.
Figure 6:
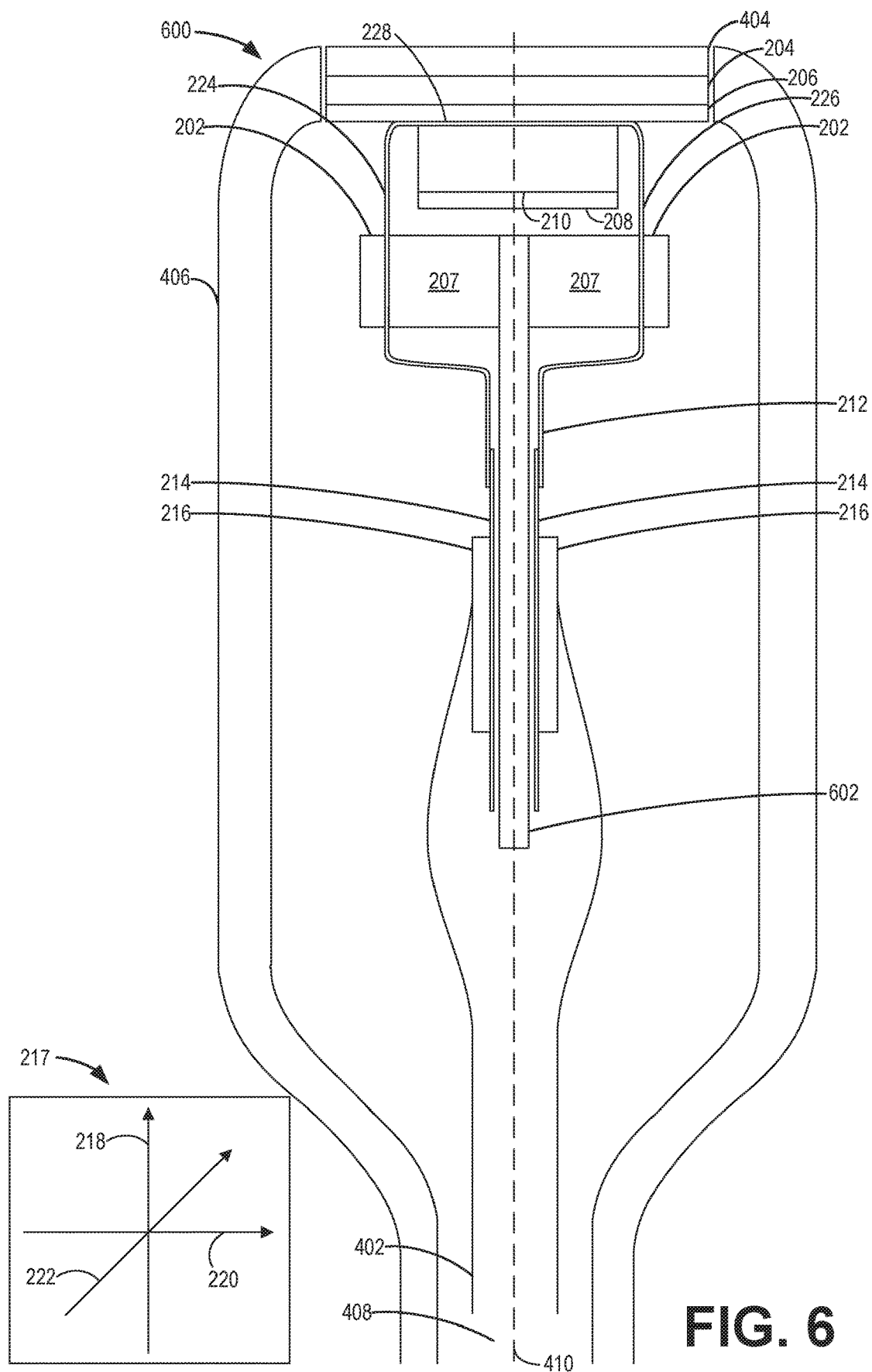
FIG. 6 shows a cross-sectional side view of a third embodiment of an ultrasound probe, in accordance with aspects of the present disclosure.

The following description relates to various embodiments of an ultrasound transducer array for an ultrasound probe of an ultrasound system, such as the system shown in FIG. 1. Embodiments of the transducer array are shown in FIGS. 2-3 and embodiments of an ultrasound probe including a transducer array are shown in FIGS. 4-6. The transducer array shown in FIGS. 2-6 may use a flexible electrical connection structure, referred to herein as a primary flex interconnect, to physically decouple electric modules and an acoustic module from one another while maintaining an electrical connection between elements of the acoustic module and the one or more electric modules. As shown in FIGS. 2-6, the electric modules may be application-specific integrated circuits (ASICs). Decoupling the electric modules from the acoustic module allows for independent module pitches, independent and thermally isolated heat sinks, and assembly on a convex structure without bending components of the electric module (e.g., ASICs), which in turn improves the functionality and reliability of the ultrasound transducer array and/or the ASICs.

Turning now to FIG. 1, a schematic diagram of an ultrasound imaging system 100 in accordance with an embodiment of the invention is seen. The ultrasound imaging system 100 includes a transmit beamformer 101 and a transmitter 102 that drive elements 104 within a transducer array, herein referred to as probe 106, to emit pulsed ultrasonic signals into a body (not shown). According to an embodiment, the probe 106 may be a one-dimensional transducer array probe. However, in some embodiments, the probe 106 may be a two-dimensional matrix transducer array probe. The components within the probe 106, including but not limited to the geometric configurations and electric connections and/or rearrangements of such components, will be discussed in greater detail below with reference to FIGS. 2-6. Still referring to FIG. 1, after the elements 104 of the probe 106 emit pulsed ultrasonic signals into a body, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including to control the input of patient data, to change a scanning or display parameter, and the like. The user interface 115 may include one or more of the following: a rotary, a mouse, a keyboard, a trackball, hard keys linked to specific actions, soft keys that may be configured to control different functions, and a graphical user interface displayed on the display device 118.

The ultrasound imaging system 100 also includes a processor 116 to control the transmit beamformer 101, the transmitter 102, the receiver 108, and the receive beamformer 110. The processor 116 is in electronic communication with the probe 106. For purposes of this disclosure, the term "electronic communication" may be defined to include both wired and wireless communications. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. A memory 120 is included for storing processed volumes of acquired data. In an exemplary embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. The image lines and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed.

In various embodiments of the present invention, one or more components of ultrasound imaging system 100 may be included in a portable, handheld ultrasound imaging device. For example, display device 118 and user interface 115 may be integrated into the exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

FIGS. 2-6 show a an ultrasound transducer array for an ultrasound probe (such as ultrasound probe 106 in FIG. 1), including a primary flex interconnect 212, that allows for decoupling various modules within the probe 106, as discussed further below. In some examples, the resultant probe that arises from such a decoupling may be probe 106 of FIG. 1. In FIGS. 2-3, an electric module (e.g., ASIC 202) and an acoustic stack 204 are seen as decoupled from one another via the primary flex interconnect 212. As used herein, "decoupled" may refer to the electric modules (ASICs 202) and acoustic module 204 being spaced apart from one another along the primary flex interconnect 212 such that they are not located at the same position on the primary flex interconnect 212. As explained further below, the electric module 202 may include an application specific integrated circuit (ASIC) and the electric module and ASIC may be referred to herein interchangeably, though alternate electric modules may be possible where ASICs are shown in FIGS. 2-6. FIGS. 2-3 also show a number of additional transducer array components interfacing with ASIC 202, acoustic stack 204, and primary flex interconnect 212, as described further below. FIGS. 4-6 show all of the components of FIGS. 2-3 arranged within an ultrasound probe, and therefore may share common features and/or configurations as those already described herein with reference to FIGS. 2-3. Regarding FIGS. 3-6, components previously introduced herein with reference to FIG. 2 are numbered identically and not re-reintroduced below.

As shown in FIG. 2, one embodiment of a transducer array 200 is shown and includes at least one ASIC 202 (multiple ASICS are shown in FIG. 2, though alternate numbers than what is depicted is possible), the acoustic stack 204, an interposer flex 206, at least one ASIC heat sink 207, an acoustic heat sink 208, an acoustic backing 210, the primary flex interconnect 212, a secondary flex interconnect 214, and at least one circuit board 216.

Additionally, FIG. 2 shows a coordinate system 217 comprising a vertical axis 218, an elevation axis 220 and a lateral axis 222 (coordinate system 217 also includes an azimuthal axis 221, depicted only in FIG. 3). The primary flex interconnect 212 may be referred to herein as the "flex interconnect". As explained above, the ASIC 202 may be referred to herein as an "electric module". Furthermore, the acoustic stack 204 may be referred to herein as an "acoustic module" or a "matrix acoustic array". Moreover, it will be appreciated that the acoustic stack 204 comprises a plurality of acoustic stack elements. For example, the acoustic stack 204 may include single or multiple rows of electrically and acoustically isolated transducer elements. Each of these transducer elements may be a layered structure including at least a piezoelectric layer and an acoustic matching layer. As will be appreciated, an electrical pulse is applied to electrodes of the piezoelectric layer, causing a mechanical change in the dimension of the piezoelectric layer. This in turn generates an acoustic wave that is transmitted towards the object. Further, when the acoustic waves are reflected back from the object, a voltage difference is generated across the electrodes that are then detected as a received signal. Thereafter, the received signal from each of the transducer elements in the acoustic stack 204 is combined and processed by the one or more ASICs 202. As explained further below, the primary flex interconnect 212 may be used to communicate electrical pulses between the piezoelectric layer and the signal processing electronics of the ASICs 202.

The primary flex interconnect 212, secondary flex interconnect 214, and interposer flex 206 may all be composed of flexible circuit material, through which the one or more ASICs 202, acoustic stack 204, and other electronic elements of the transducer array (such as circuit board 216), may form their respective electrical connections to the probe as a system, and also to various components within the probe. For example, looking at FIG. 2, the acoustic stack 204 may be electrically connected with any of the ASICs 202 by sharing a common electrical connection, as provided in FIG. 2 by the interposer flex 206 being coupled to primary flex interconnect 212, and each of these interconnects (i.e., interposer flex 206 and primary flex interconnect 212) being coupled to at least one of the acoustic stack 204 and ASICs 202. The primary flex interconnect 212 and secondary flex interconnect 214 may act as a type of support structure to conform to the shape of the ultrasound probe, and to support the electric and acoustic modules (such as ASICs 202 and acoustic stack 204, respectively). Furthermore, the primary flex interconnect 212 and secondary flex interconnect 214 may be coupled with components and/or in electrical sharing contact with components of the transducer array on all faces of the flex interconnect. It will be appreciated that each of the flex interconnects (primary flex interconnect 212, secondary flex interconnect 214, and interposer flex 206) may be flexible and adaptable to provide electrical connection between elements of an acoustic array (such as, acoustic stack 204) and a circuit board 216 and/or interface board. Each of the flex interconnects may include a plurality of isolated electrical connections for electrically coupling two electrical components to one another. For example, the primary flex interconnect 212 may include a plurality of electrical connections (e.g., traces) that run through the primary flex interconnect 212 and electrically couple the individual piezoelectric transducer elements of the acoustic stack 204 to the ASICs 202. As seen in FIG. 2, though the ASICs 202 and the acoustic stack 204 are spaced physically away from one another (and positioned in different planes), they remain electrically coupled to one another via the electrical connections of the primary flex interconnect 212. As used herein, the term "flex interconnect" may be used to refer to any flexible circuit material, including the primary flex interconnect 212, secondary flex interconnect 214 and interposer flex 206, that forms electrical connections between electrical components coupled to a surface of the flex interconnect.

Returning to the drawings and referring to FIG. 2, a transducer array having decoupled electric and acoustic modules, in accordance with aspects of the present disclosure, is depicted. The transducer array 200 is typically used to transmit ultrasonic or acoustic waves towards an object (not shown in FIG. 1). In response to transmitting the ultrasonic waves, the transducer array 200 may receive reflected or attenuated ultrasonic waves from the object. Further, these received ultrasonic waves are processed to obtain an ultrasonic image of the object. In one embodiment, the object may be a region of interest in a patient.

As shown in FIG. 2, the transducer array 200 is comprised of six ASICs 202 and one acoustic stack 204, referred to herein as electric modules and an acoustic module, respectively. Each of these electric and acoustic modules may be interchangeable on the support structure, the primary flex interconnect 212, and thus, the electric and acoustic modules may not be required to be located in a particular position on the primary flex interconnect 212. Said another way, the electric and acoustic modules may be positioned at different locations on the primary flex interconnect 212 than shown in FIG. 2. In addition, if one of these electric and/or acoustic modules is affected or damaged, then it may be replaced by a new electric and/or acoustic module.

As shown in FIGS. 2-6, the primary flex interconnect 212 is a curved structure with several planar or curved sides that transition between one another via a curved transition. Said another way, the primary flex interconnect 212 is bent in several locations and forms several sides. In the embodiment of FIG. 2, the ASICs 202 and acoustic stack 204 are detachably coupled to a portion (e.g., sides) of the supporting primary flex interconnect 212. The coupling interface between the primary flex interconnect 212 and the ASICs 202 and/or acoustic stack 204 may be comprised of solder, anisotropic conduct film (ACF), or the like. The portion of the supporting primary flex interconnect 212 that is coupled to the ASICs 202 and acoustic stack 204 may be a planar structure, that acts as a base or spine for the ASICs 202 and acoustic stack 204. It will be appreciated that in FIGS. 2-6, the portion of the primary flex interconnect 212 that is coupled above (relative to vertical axis 218) the acoustic backing 210 and acoustic heat sink 208, may be referred to as a top side 228 of the primary flex interconnect 212, wherein the top side is connected between a first side 224 and second side 226 of the primary flex interconnect 212. As shown in FIG. 2, the ASICs 202, ASIC heatsinks 207 and secondary flex interconnect 214 are coupled to the first and second 224, 226 sides of the primary flex interconnect 212. Furthermore, when the top side 228 of primary flex interconnect 212 is planar in nature (as seen in FIGS. 2, 4, and 5), it is arranged perpendicular to the planar first and second sides 224, 226 of the primary flex interconnect 212 (note that the first side 224 and second side 226 are parallel to one another). Moreover, when the top side 228 of the primary flex interconnect 212 is curved and coupled along with the curved acoustic stack 204 (as seen in FIG. 3), the portions of the first and second sides of the primary flex interconnect 212 that are coupled to the ASICs 202, ASIC heat sinks 207 and secondary flex interconnects 214 are also planar, and parallel to one another. It will be appreciated that because ASICs 202 and acoustic stack 204 are coupled to the same substrate (primary flex interconnect 212), and because they may be moved around on the shared substrate, that a large number of potential transducer array geometries thereby exist. The mobility of these components (ASICs 202 and acoustic stack 204), and their ability to be mobilized independent of one another (e.g., being decoupled from one another), may aid in designing and manufacturing a desired ultrasound probe. For example, the ASICs 202 and acoustic stack 204 may be arranged on the supporting primary flex interconnect 212 to form a portable ultrasound probe with a curved transducer array, without fear of damage to the ASIC 202 components (described in greater detail below).

In addition, the ASICs 202 and acoustic stack 204 may be arranged on one or more types of support structures, flexible circuit materials, and flex interconnects (such as interposer flex 206, primary flex interconnect 212, and secondary flex interconnect 214), in order to conform to the desired shape of the ultrasound probe during manufacturing. For example, as seen in FIG. 2, if the acoustic stack 204 is arranged on a relatively flat portion of its supporting structures (interposer flex 206, primary flex interconnect 212, acoustic backing 210) a flat transducer array may be formed. In another example, as seen in FIG. 3, if the acoustic stack 204 is arranged on a convex portion of the supporting structures (such as interposer flex 206, primary flex interconnect 212, and acoustic backing 210) a convex transducer array may be formed. It should be noted that the transducer array 200 may include any number of electric modules, and is not limited to the number of ASICs 202 shown in and of FIGS. 2-6. However, for each primary flex interconnect 212, there may be only one acoustic stack 204 and one or more ASICs 202 electrically coupled to the single acoustic stack 204 through the primary flex interconnect 212.

As previously mentioned, the acoustic stack 204 (e.g., matrix acoustic array) is configured to send one or more acoustic waves towards an object during an ultrasound session. In response, the acoustic stack 204 may receive the reflected acoustic waves from the object. These acoustic waves may have a frequency in a range from about 0.5 MHz to about 25 MHz. In one embodiment, the acoustic stack 204 includes single or multiple rows of electrically and acoustically isolated transducer elements. In one embodiment, the acoustic stack 204 may include micromachined ultrasound transducers, such as capacitive micromachined ultrasonic transducers (cMUTs) and/or piezoelectric micromachined ultrasonic transducers (pMUTs).

As will be appreciated, an electrical pulse is applied to electrodes of the piezoelectric layer (not shown) of acoustic stack 204, causing a mechanical change in the dimension of the piezoelectric layer. This in turn generates an acoustic wave that is transmitted towards the object. Further, when the acoustic waves are reflected back from the object, a voltage difference is generated across the electrodes of the acoustic stack 204 that are then detected as a received signal. Thereafter, the received signal from each of the transducer elements in the acoustic stack 204 is combined and processed by the ASIC 202 through the electrical connection provided in tandem by primary flex interconnect 212 and interposer flex 206.

The acoustic stack 204 is directly coupled to a first side 224 of the interposer flex 206. A second side 226 of the interposer flex 206, opposite the first side 224 is coupled to the primary flex interconnect 212. As introduced above, the primary flex interconnect 212 is used for providing electrical connection between the acoustic stack 204 and signal processing electronics (e.g., ASICs 202) or circuit board 216 that is disposed within a body of the ultrasound probe.

Further, a first surface of the primary flex interconnect 212 is coupled directly to the acoustic backing 210. The ASICs 202 and interposer flex 206 are each directly coupled to a second surface, opposite the first surface, of the primary flex interconnect 212. In this way the primary flex interconnect 212 is positioned between the interposer flex 206 and the acoustic backing 210. In alternative embodiments, interposer flex 206 may be omitted, so that the acoustic stack 204 is coupled directly to a first face of the primary flex interconnect 212, with a second, opposite face of the primary flex interconnect 212 coupled to acoustic backing 210. Returning to FIG. 2, the acoustic heat sink 208 is coupled directly to the acoustic backing 210, on an opposite side of the acoustic backing 210 than the side coupled directly to the primary flex interconnect. Looking at FIGS. 2-6, it may be seen that the acoustic heat sink 208 is positioned away from ASIC heat sink 207, and that the two are not in direct contact and/or coupled together. Spacing the acoustic heat sink 208 and ASIC heat sink 207 apart from one another further helps to decrease heat transfer within the system (such as systems 200, 300, 400 and 500 of FIGS. 2, 3, 4 and 5, respectively). Furthermore, at least one of acoustic heat sink 208 and ASIC heat sink 207 may be outfitted with a thermal isolation element and/or layer (not shown) that is arranged between a first heat sink (e.g., acoustic heat sink 208) and a second heat sink (e.g., ASIC heatsink 207). In embodiments where the transducer array is outfitted with multiple ASIC heat sinks 207 (such as the multiple ASIC heat sinks 207, of FIG. 2), it will be appreciated that the thermal isolation element and/or layer may serve to isolate a first heat sink (e.g., acoustic heat sink 208) from multiple second heat sinks (such as, the multiple ASIC heat sinks 207, of FIG. 2).

Returning to FIG. 2, the acoustic backing 210 may be configured to absorb and/or scatter the acoustic waves or energy that is transmitted in a direction away from the object being scanned. Particularly, the acoustic waves are generated by the piezoelectric layer. Further, a portion of the generated acoustic waves may be reflected from structures or interfaces behind the transducer array. These acoustic waves may combine with the acoustic waves that are reflected from the object, which in turn reduces the quality of the ultrasonic image of the object.

To avoid the above problem, the acoustic backing 210 may be positioned beneath the acoustic stack 204 to attenuate or absorb the acoustic waves that are propagated in the reverse direction to the object. In one example, the acoustic backing 210 may include acoustic backing materials that are combinations of a high-density acoustic scatterer, such as tungsten metal, and/or a soft acoustic absorbing material, such as silicone, in a matrix of an epoxy or a polyurethane. In another example, acoustic backing 210 may include acoustic backing materials that are thermal fillers, such a boron nitride, or inlays made from graphite or metal to increase thermal conductivity. In yet another example, the backing material may comprise an epoxy filled graphite foam which has the added advantage of having a high thermal conductivity to draw heat away from the acoustic stack 204. Also, the acoustic heat sink 208 may be configured to absorb or dissipate the heat generated in the acoustic module 204.

In one embodiment, the acoustic heat sink 208 along with the acoustic backing 210 may be configured to absorb the heat generated in the acoustic stack 204 and transfer heat away from the elements of the acoustic stack 204. In one embodiment, the acoustic backing 210 may be coupled above (with respect to vertical axis 218) acoustic heat sink 208, with all other components in the same previously described positions. In another embodiment, the acoustic heat sink 208 may be coupled above (according to vertical axis 218) acoustic backing 210, with all other components in the same previously described positions. In yet another embodiment, the acoustic backing 210 and acoustic heat sink may be integrated into a single component.

As seen in FIG. 2, the top side 228 of the primary flex interconnect 212 that is coupled to the acoustic backing 210 extends past the edge of the acoustic backing 210 where it then curves downward (according to vertical axis 218) continuously to form the first side 224 and second side 226, which are parallel to one another and perpendicular to top side 228. The first and second sides 224, 226 of the primary flex interconnect 212 are where the ASICs 202 and ASIC heat sinks 207 may couple to. For example, as seen in FIG. 2, the ASICs 202 are coupled to a first surface of the primary flex interconnect 212, and the ASIC heat sinks 207 are coupled to the opposite, second surface of the primary flex interconnect 212. As such, the first and second sides 224, 226 of the primary flex interconnect 212 are positioned between each ASIC 202 and corresponding ASIC heat sink 207. Alternative embodiments may have different numbers of ASICs 202 and ASIC heat sinks 207, and those components may be arranged differently from FIG. 2. For example, a transducer array may have four ASICs 202 and four ASIC heatsinks 207, with the same coupling pattern to primary flex interconnect 212 as mentioned above, but have three ASICs 202 and three corresponding ASIC heat sinks 207 on the first side 224 and one ASIC 202 and one corresponding ASIC heat sink 207 on the second side 226.

As seen in FIG. 2, the primary flex interconnect 212 may be directly coupled on at least one face to a secondary flex interconnect 214. The secondary flex interconnect 214 is directly coupled to one or more circuit boards 216, thereby putting the circuit board(s) 216 in electric communication with the rest of the electrical components (acoustic stack 204, ASICs 202) of the transducer array 200. Furthermore, the coupling between primary flex interconnect 212, secondary flex interconnect 214, and circuit boards 216 may present as detachable or permanent. Circuit boards 216 may transmit and/or receive beamforming and/or multiplexing, support secondary electronics such as voltage regulators and voltage capacitors, and control circuits for ASICs 202, as discussed in greater detail in FIG. 4.

Looking at FIG. 2, the secondary flex interconnect 214 is coupled to the primary flex interconnect 212 via overlapping segments of the secondary flex interconnect 214 and primary flex interconnect 212. The overlapping segment of the secondary flex interconnect 214 is positioned outward of the overlapping segment of the primary flex interconnect 212, relative to a center of the transducer array. In alternative embodiments, the primary flex interconnect 212 and secondary flex interconnect 214 may be coupled in a various number of geometries. For example, the overlapping segment of primary flex interconnect 212 may be positioned outward of the overlapping section of the secondary flex interconnect 214, relative to the center of the transducer array, where the overlapping segments are defined as the portions of the flex interconnects that are coupled together. In another embodiment, the secondary flex interconnect 214 may be rigid. In yet another embodiment, secondary flex interconnect 214 may be omitted, so that the primary flex interconnect 212 directly interfaces with circuit boards 216. For example, the first and second sides 224, 226 of the primary flex interconnect 212 may be extended in vertical length (as defined by vertical axis 218) to create more surface area for coupling to circuit boards 216, so that the overall size of the transducer array is unchanged.

Thus, by using the ASICs 202 and acoustic stack 204 in conjunction with flexible circuit material (e.g., primary flex interconnect 212, secondary flex interconnect 214, and interposer flex 206) the transducer array 200 may be formed into the shape of the ultrasound probe while providing electrical connections between each of the electrical components of the transducer array.

Turning to FIG. 3, a curved transducer array 300 is seen. All of the same components seen in FIG. 2 are present in FIG. 3, with no new transducer array components being introduced. The primary difference between transducer arrays 200 and 300, lies in the geometries of the acoustic stacks 204, interposer flex 206, and primary flex interconnect 212. In FIG. 2 a linear transducer array 200 was generated, in part, by the planar (relative to lateral axis 222) nature of the acoustic stack 204, and acoustic backing 210. Looking at FIG. 3, it may be seen that while the rectangular dimensions of the acoustic stack 204 and interposer flex 206 remain consistent, both components have gained an azimuthal arch (relative to azimuthal axis 221) that is at peak height (relative to vertical axis 218) at the lateral (relative to lateral axis 222) center of both components, and consistently diminishes in height to a global minima at the terminal ends of both components.

Still looking at FIG. 3, it may be seen that the primary flex interconnect 212 does not drape in the same way as it did in FIG. 2. Owing to the planar coupling between the components located vertically above and below the top side 228 of primary flex interconnect 212, the primary flex interconnect 212 of FIG. 2 drapes off the acoustic backing 210 in a perpendicular fashion. That is, the portion of the primary flex interconnect 212 of linear transducer array 200 that is coupled vertically above the acoustic backing 210 lays laterally planar and thus perpendicular to the segments (e.g., sides) of the primary flex interconnect 212 that drape in a planar fashion off the edge of the acoustic backing 210. Looking at FIG. 3, it can be seen that the arched geometry of the acoustic stack 204 and interposer flex 206 contribute to a billowing shape in the primary flex interconnect 212, as the flex interconnect drapes off the edge of the acoustic backing 210.

Looking at FIGS. 2 and 3, it may be seen that while the portion of the primary flex interconnect 212 that is coupled to the acoustic stack 204 may be curved (as seen in FIG. 3) or planar (as seen in FIG. 2) according to a desired curved or planar shape of the acoustic stack 204, the portions of the primary flex interconnect 212 that are coupled to the ASICs 202 are planar in both FIGS. 2 and 3, since bending the ASICs 202 may result in damage to the ASICs 202. Decoupling the ASICs 202 from the acoustic stack 204, thus allows for a curved or flat transducer array with one or more ASICs 202 (such as transducer arrays 300 and 200, seen in FIGS. 3 and 2, respectively) that are maintained in a relatively flat plane (thereby preserving the electronic function of the ASICs 202).

While FIG. 2 and FIG. 3 show exemplary embodiments for a linear transducer assembly and curved transducer assembly, respectively, a number of other transducer array geometries are possible. By varying the number and geometric configurations of the electric and acoustic modules, and by altering the shape of the acoustic stack and interposer flex as needed, it possible to achieve any number of desired probe shapes during manufacturing.

Referring now to FIG. 4, a cross-sectional, side view of an ultrasound probe is depicted. The ultrasound transducer probe 400 includes a transducer array having an acoustic stack 204 and ASICs 202 that are coupled to a supporting primary flex interconnect 212, on the top side 228 of the primary flex interconnect 212 and on the first and second sides 224, 226 of the primary flex interconnect 212, respectively. In addition to primary flex interconnect 212, transducer probe 400 of FIG. 4 includes secondary flex interconnect 214 and interposer flex 206. Each of the flex interconnects (primary flex interconnect 212, secondary flex interconnect 214 and interposer flex 206) may be flexible and adaptable to provide electrical connection between an acoustic array (referred to herein as acoustic stack 204) and an interface/circuit board (such as ASIC 202 and circuit board 216), as explained above.

Looking at FIG. 4, primary flex interconnect 212 provides electrical connection between the circuit/interface boards (such as, ASICs 202 and circuit board 216) and acoustic stack 204 via interposer flex 206. Particularly, the primary flex interconnect 214 of FIGS. 2-6 is disposed between an acoustic array (i.e., acoustic stack 204, via interposer flex 206) and an ASIC 202 layer, while the secondary flex interconnect 214 is electrically coupled between the primary flex interconnect 212 and a circuit board 216. Looking at FIGS. 2-4, it may be seen that while there is one primary flex interconnect 212 component, there are two secondary flex interconnect 214 components, with one secondary flex interconnect 214 coupled to the first side 224 of primary flex interconnect 212, and the second secondary flex interconnect 214 coupled to the second side 226 of primary flex interconnect 212. In an alternative embodiment, there may be only one flex interconnect type (e.g., primary flex interconnect 212) that couples all of the components (e.g., ASICS 202, circuit boards 216, acoustic stack 204, etc.) together, instead of two (e.g., primary flex interconnect 212 and secondary flex interconnect 214). In yet another embodiment, both primary flex interconnect 212 and secondary flex interconnect 214 may be used to couple all of the components together, however, the secondary flex 214 may appear as one continuous unit (as seen in FIG. 5) as opposed to two or more individual units (as seen in FIGS. 2-4).

In addition, the secondary flex interconnect 214 may have different shapes depending on the position of the electric and acoustic modules on the support structure of the probe (including the primary flex interconnect 212). For example, as seen in FIGS. 2 and 4, if the acoustic stack 204 is generally planar in nature (e.g., not curved), the secondary flex interconnect 214 has a relatively straight or unbent shape and is coupled to the primary flex interconnect 212. In another example, as seen in FIG. 5, the first and second sides 224, 226 of the primary flex interconnect 212 closest to top side 228 are parallel to one another and perpendicular to top side 228, before diverting perpendicularly toward centerline 410 so that they are level with one another (with reference to elevation axis 220), before diverting a final time to resume a parallel relationship when the first and second sides 224, 226 come into contact and couple with secondary flex interconnect 214 arranged in a continuous, rectangular pathway (as seen in FIG. 5). Thus, one of many different shapes of the secondary flex interconnect 214 may be selected to couple the primary flex interconnect 212 to the circuit board 216.

Returning to FIG. 4, the transducer array components of FIGS. 2-3 are arranged in conjunction with several additional components, namely, a lens 404, coaxial probe cable 402, probe cable assembly 408, and housing 406 for the probe.

Looking at FIG. 4, housing 406 comprises a tubular structure extending downward in the vertical direction (as per vertical axis 218) from lens 404. Housing 406 supports lens 404 while enclosing the components of the transducer array (such as transducer array 200 of FIG. 2), coaxial probe cable 402, and probe cable assembly 408. Housing 406 provides a structure by which a user may manually grip and manipulate probe 400. In other embodiments, depending upon what portion of an anatomy for which ultrasound probe 400 is to be used, housing 406 may have other sizes, shapes and configurations.

Probe cable assembly 408 extends in a downward fashion (in the vertical direction, starting from lens 404, as per vertical axis 218) from housing 406 to guide and receive coaxial probe cable 402. Probe cable assembly 408 serves as a strain relief to relieve strain during flexing or bending of coaxial probe cable 402 as a result of manipulation of ultrasound probe 400. In other implementations, a probe cable assembly 408 may be omitted. For example, in other implementations, ultrasound probe 400 may communicate with external display devices and/or external analysis devices in a wireless fashion using a wireless antenna contained within housing 406. In such an implementation, power may be supplied to probe 400 using a rechargeable battery. In such an implementation, probe cable assembly may be omitted.

Lens 404 comprises an acoustic lens to focus emitted sound waves. Although illustrated as being a generally planar rectangle, in other implementations, lens 404 may have other configurations. For example, lens 404 may alternatively be a linear cylinder in an alternative embodiment. In yet another alternative embodiment the lens 404 may be a curved cylinder, such as in implementations where probe 400 comprises an abdominal probe or where probe 400 comprises an endocavity probe. While lens 404 is depicted as being the most outer facing component of probe 400, it will be appreciated that in alternative embodiments additional components may be coupled to the exposed face of lens 404, such as a probe nose. For example, a nose may partially enclose and support lens 404 and be comprised of an outer polymeric casing wall in thermal contact with one or more of acoustic heat sink 207 and ASIC heat sink 208, in order to siphon heat away from lens 404.

Looking at FIG. 4, it may be seen that lens 404 is coupled to and in face sharing contact with acoustic stack 204, located vertically below lens 404. As previously discussed, the acoustic stack 204 comprises an ultrasound device located at a front end (defined as the end of the probe with lens 404) of probe 400 that is configured to emit and receive ultrasonic sound waves. During imaging by probe 400, the lens 404 of probe 400 may be placed upon or against the exterior of anatomy, or may be partially inserted into anatomy depending upon those portions of the anatomy which are to be imaged. In one implementation, acoustic stack 204 comprises piezoelectric crystals and ceramic that change shape in response to the application electrical pulse so as to produce vibrations or sound waves. Likewise, the impact of sound or pressure waves upon such crystals produces electrical currents. The interposer flex 206 is coupled to and in face sharing contact with the face of the acoustic stack 204 that is opposite the lens 404. As shown in FIGS. 2 and 3, and now FIG. 4, the interposer flex 206 allows electrical communication between acoustic stack 204 (which is coupled to the top most face of the interposer flex 206) and primary flex interconnect 212 (which is coupled to the bottom most face of the interposer flex 206).

Returning to primary flex interconnect 212 of FIG. 4, it may be seen that the primary flex interconnect 212 has the same coupling relationship to acoustic backing 210 as described in FIGS. 2-3, that is, the primary flex interconnect 212 is coupled to and in face sharing contact with acoustic backing 206 opposite the face that is coupled to and in face sharing contact with interposer flex 206. Acoustic backing 210 is then coupled to acoustic heat sink 208, so that a face of the acoustic backing 210 is coupled to and in face sharing contact with a first surface of the primary flex interconnect 212. In this way, the acoustic backing 210 and acoustic heat sink 208, are directly above/below one another, relative to vertical axis 218. As in FIGS. 2-3, the geometric arrangement of acoustic backing 210 being located vertically above acoustic heat sink 208 is interchangeable, and in some embodiments, the two components may even be combined into one component. Additionally, the acoustic backing 210 paired with the acoustic heat sink 208 may be considered and referred to herein as a single base unit. The acoustic backing 210 may be used to eliminate back reflections from the probe itself and lens 404 may be used to focus emitted sound waves.

Returning to the discussion of the primary flex interconnect 212 shown in FIG. 4, located along the first and second sides 224, 226 of the primary flex interconnect 212 that drape off of acoustic backing 210, it can be seen that two ASICs 202, spaced apart from one another, are coupled to the face of the primary flex interconnect 212 that is closest to housing 406 (which may also be referred to as the most outward facing face of the first and second sides 224, 226 of primary flex interconnect 212, along elevation axis 220 and relative to a centerline 410 of the probe). On the opposite face of the first and second sides 224, 226 of primary flex interconnect 212 (that is to say, on the most medial faces of the first and second sides 224, 226, along elevation axis 220 and relative to the centerline 410), it can be seen that ASIC heat sinks 207 are coupled to the primary flex interconnect 212 in locations corresponding to where ASICs 202 can be found on the opposite face of the primary flex interconnect 212. In this way, a heat sink 207 is coupled to a first face (e.g., surface) of the primary flex interconnect 212 and a corresponding ASIC 202 is coupled to a second face, opposite the first face) of the primary flex interconnect 212. As a result, the heat sink 207 may transfer heat away from the corresponding ASIC 202 which is arranged directly opposite the heat sink 207 across the primary flex interconnect 212.

The primary flex interconnect 212 puts the ASICs 202 in electrical communication with every other electronic component coupled to a flex interconnect (primary flex interconnect 212, secondary flex interconnect 214, interposer flex 206). Additionally, the primary flex interconnect 212 does not interfere with the transfer of heat from a corresponding ASIC 202 to ASIC heat sink 207. Acoustic heat sink 208 and ASIC heat sink 207 are formed from one or more materials having a thermal resistance less than a thermal resistance of the primary flex interconnect 212, interposer flex 306, and acoustic backing 210. For purposes of this disclosure, two members are "thermally coupled" when one or more intermediate heat conducting structures (such as primary flex interconnect 212, interposer flex 206, and acoustic backing 210) form a bridge or a series of structures, wherein the bridge or series of structures is in contact with the two members and continuously extending between the two members to conduct heat between the two members. In one embodiment, acoustic heat sink 208 and ASIC heat sinks 207, comprise a metal, such as aluminum. In other embodiments, thermal acoustic heat sink 208 and ASIC heat sinks 207 may comprise other metals or other materials having thermal resistivity that is less than that of the housing 406. Because heat is continuously and uniformly dissipated away from the acoustic stack 204 and ASICs 202, across flex interconnects to acoustic heat sink 208 and ASIC heat sinks 207, respectively, surface temperature regulations for the ultrasound probe may be more easily satisfied. As a result, additional energy may be directed into a patient's anatomy by probe 400 for enhanced image capture and quality while still satisfying regulatory requirements such as acoustic output or surface temperature regulations It will be appreciated that decoupling each of the electric modules (e.g., ASICs 202) from the acoustic module (e.g., acoustic stack 204) (via spacing them apart from one another along the primary flex interconnect 212 such that they are not aligned with one another at the same vertical position along the elevation axis 220) is what allows for independent heat sinks for the electric and acoustic modules, which thereby increase the amount of additional energy that may be directed into a patient's anatomy by probe 400, as stated above. It will also be appreciated that while ASIC heat sink 207 is depicted as having a larger peripheral boundary (and therefore larger size, in general) than ASIC 202 in FIG. 4, that alternative embodiments may have an ASIC heat sink 207 that is the same size, smaller, the same shape as, or a different shape than the corresponding ASIC 202. Furthermore, while the geometric arrangement of ASICs 202 and ASIC heat sinks 207 have already been described for FIG. 4, relative to the faces of the first and second sides 224, 226 of the primary flex interconnect 212 that are doing the coupling, alternative embodiments may show any number of ASIC 202 and ASIC heat sink 207 rearrangements. For example, these two components may switch positions, if spacing within probe 400 allows, so that the ASIC heat sink 207 is on the face of the first and second sides 224, 226 of the primary flex interconnect 212 that is closest to housing 406, and the ASIC 202 is aligned with ASIC heat sink 207, but on the opposite face of the first and second sides 224, 226 of primary flex interconnect 212. In yet another embodiment, there may be no primary flex interconnect between the two components, and they may be directly coupled, in part, to one another, as seen in FIG. 5 and discussed further below.

Returning once more to the discussion of the primary flex interconnect 212, at the most downward portion (according to vertical axis 218) of the primary flex interconnect 212, there is a coupling that results in an overlap between a portion of the primary flex interconnect 212 and a portion of the secondary flex interconnect 214, such that the bottom-most portion of primary flex interconnect 212 is internal relative to the top-most portion of secondary flex interconnect 214 (which is closer to housing 406 than primary flex interconnect 212, and thus referred to as facing outward), relative to the centerline 410. Still looking to FIG. 4, it may be seen that a first end of each of the two secondary flex interconnects 214 depicted is coupled to one of the first side 224 and second side 226 of the primary flex interconnect 212. A second end of each of the two secondary flex interconnects 214 shown in FIG. 4 is coupled to one of the two circuit boards 216 wherein coaxial probe cable 402 is coupled to each of the two circuit boards 216. As in FIGS. 2-3, coupling between primary flex interconnect 212 and secondary flex interconnect 214 puts the two in electrical communication with one another and allows any electrical component (such as ASIC 202, acoustic stack 204, or circuit board 216) coupled to primary flex interconnect 212 or secondary flex interconnect 214 to also be in electrical communication with one another. As such, electrical signals may pass from the acoustic stack 204 to each ASIC 202, through the primary flex interconnect 212. Electrical signals may then pass from each ASIC to a corresponding circuit board 216 through both the primary flex interconnect 212 and the secondary flex interconnect 214. As explained above, both the primary flex interconnect 212 and secondary flex interconnect 214 may each include a plurality of electrical traces that connect individual transducer elements of the acoustic stack 204 to corresponding elements in the ASICs 202 and then the circuit boards 216.

Ultrasound probe 400 also comprises a controller configured to control operation of the probe 400, though it will be appreciated that as used herein, controller is a general term, and the acts of which may be carried out by multiple sub-components, such as circuit boards 216 and ASICs 202. For example, the controller may generate control signals controlling and directing emission of ultrasound waves by acoustic stack 204. The controller may additionally facilitate the supply of power to acoustic stack 204 as well as the transmission of signals from ultrasound probe 400 to an external computing device for analysis and display. In one embodiment, the controller may comprise a printed circuit board supporting one or more electronic components, such as electrical tuning components, communication components and other components for carrying out such functions, such as circuit board 216 in FIG. 4. In another embodiment, the controller may, at least in part, comprise an ASIC supported on a printed circuit board. In yet another embodiment, the ASIC may use Redistributed Chip Packaging (RCP) to simplify routing and use different and/or multiple ASICS on the same flex interconnect. In another implementation, the controller may comprise one or more processing units and an associated memory (not shown), wherein the one or more processing units follow instructions contained in the associated non-transitory computer-readable medium of the memory to perform or carry out such functions as the supply of power to acoustic and electric modules within probe 400, the control of the emission of ultrasound waves by acoustic stack 204, and the transmission of signals representing sensed ultrasound reflections from the anatomy of the patient to various components within the ultrasound system (such as the components described in FIG. 1 of ultrasound imaging system 100).

Coaxial probe cable 402 comprises an elongate cable connected to circuit board 216 to supply power to ultrasound probe 400, to transmit control signals from an external source to controlling components within the probe 400 (such as circuit board 16 and ASICs 202) for the control of probe 400, and to transmit data signals from ultrasound probe 400 to an external processor, display, and/or analysis system. As noted above, in other implementations, coaxial probe cable 402 may be omitted where such external communication is performed in a wireless fashion and where power is supplied by a battery, such as a rechargeable battery. In such an implementation, housing 406 may be slightly reconfigured to facilitate insertion or replacement of the battery.

Turning to FIG. 5, an alternative cross-sectional, side view of an ultrasound probe 500, in accordance with aspects of the present disclosure, is depicted. Ultrasound probe 500 contains precisely the same components arranged in a slightly different geometric configuration than those in ultrasound probe 400. Components and/or features and/or configurations already described above with reference to FIGS. 2-4, therefore continue to be numbered identically and are not reintroduced below.

Looking at FIG. 5, the transducer array components of FIGS. 2-3 are arranged in conjunction with lens 404, coaxial probe cable 402, probe cable assembly 408, and housing 406 for the probe 500 (as they were in FIG. 4). Looking at the uppermost (according to vertical axis 218) portion of probe 500, it is apparent that the lens 404, acoustic stack 204, and interposer flex 206 have maintained relatively the same geometric configuration. That is, all three components have maintained the same coupling pattern and have boundaries (e.g., and thus lengths in a direction of the elevation axis 220) that are identical. In alternative embodiments the lens 404, acoustic stack 204, and interposer flex 206 may have non-identical boundaries. For example, the interposer flex 206 may still be coupled beneath acoustic stack 204 in an alternative embodiment, but the interposer flex 206 may be larger, with a boundary exceeding beyond the perimeter of acoustic stack 204.

Looking at primary flex interconnect 212 of FIG. 5, it can be seen that a different geometric pattern has arisen, at least in part, due to the smaller peripheral boundary imposed by the base unit (i.e., acoustic backing 210 and acoustic heat sink 208), which are arranged in the same coupling pattern as in FIG. 4, but appear smaller in size than in FIG. 4 (when compared to the uniform peripheral boundary of lens 404, acoustic stack 204 and interposer flex 206 with acoustic backing 210 and acoustic heat sink 208, as seen in FIG. 4). As a result of the top side 228 of primary flex interconnect 212 taking up less surface area, the first and second sides 224, 226 of the primary flex interconnect 212 beginning draping (e.g., curving downward) earlier in FIG. 5 than in FIG. 4, and the coupling of additional probe 500 components (such as ASIC 202) to the first and second sides 224, 226 of the primary flex interconnect 212 in FIG. 5 is affected, leading to a variance in the geometry of probe 500 compared to probe 400.

Continuing along the vertically draped portion of the first and second sides 224, 226 of the primary flex interconnect 212 of FIG. 5, it can be seen that two ASICs 202 of probe 500 are coupled to the most outwardly facing faces (e.g., surfaces) of the first and second sides 224, 226 of the primary flex interconnect 212 (i.e., the faces of the first and second sides 224, 226 that are closest to housing 406). Owing to size constraints within probe 500, the ASIC heat sinks 207 associated with ASICs 202 do not fit on the opposite face of the first and second sides 224, 226 of the primary flex interconnect 212, and are instead coupled to the opposite face of the ASICs 202, such that each ASIC 202 is sandwiched between the primary flex interconnect 212 (at the most medial facing face of the ASIC 202, along elevation axis 220 and relative to centerline 410) and a corresponding ASIC heat sink 207 (at the most lateral facing face of the ASIC 202, along elevation axis 220 and relative to the centerline 410). As such, each ASIC 202 is in face-sharing contact with both the primary flex interconnect (at a first face of the ASIC 202) and a corresponding ASIC heat sink 207 (at a second face, opposite the first face, of the ASIC 202). While the ASIC heat sinks 207 are depicted as being in face sharing contact with and coupled to housing 406 in FIG. 5, it will be appreciated that the ASIC heat sinks 207 may, in some embodiments, not be coupled to or in face sharing contact with housing 406, and may instead be coupled to other support structures or components of probe 500 (not shown), or not be coupled to any component or support structure of probe 500 at all (excluding corresponding ASIC 202 components, through either direct or indirect contact).

Continuing along the vertically draped portion (as per vertical axis 218) of the first and second sides 224, 226 of the primary flex interconnect 212 of FIG. 5, it can be seen that the primary flex interconnect 212 curves inwards (relative to housing 406) from both ends in a horizontal fashion (defined by a horizontal axis that is interchangeable with elevation axis 220) towards one another, until coming into contact with a closed rectangular loop of secondary flex interconnect 214 material. Having come into contact with secondary flex interconnect 214, the first and second sides 224, 226 of primary flex interconnect 212 then change direction in a perpendicular fashion once more, to continue in a vertically downwards (as per vertical axis 218) direction until termination. The resultant vertical portions of both the primary and secondary flex interconnects 212, 214 that overlap and are parallel to one another are coupled and thereby in electrical communication with one another. Picking up at the site where the primary and secondary flex interconnects 212, 214 are coupled to each other (e.g., a first end of the second flex interconnect 214), and continuing downwards along the single secondary flex interconnect 214, it is seen in FIG. 5 that a second end of the secondary flex interconnect 214 is coupled to two circuit boards 216, on its most outward facing face (that is, the face of secondary flex interconnect 214 that is closest to housing 406). It will be appreciated that in FIG. 5 one secondary flex interconnect 214 may be used to electrically couple circuit boards 216 to primary flex interconnect 212, as opposed to FIGS. 2-4 where two secondary flex interconnects 214 were used to accomplish the same goal of electrically coupling circuit boards 216 to primary flex interconnect 212. Alternative embodiments may utilize one, two, or more secondary flex interconnects 214 to connect one or more circuit boards to a primary flex interconnect and associated components of the primary flex interconnects (e.g., ASICs, acoustic stacks, etc.).

As in FIG. 4, coaxial probe cable 402 comprises an elongate cable connected to circuit boards 216, which serves the same functions as those described above in FIG. 4. It will be appreciated that the secondary flex interconnect 214 of FIG. 5 is connected to the same components as in FIG. 4, the two differences being that instead of appearing as two components (as in FIG. 4), the secondary flex interconnect 214 is connected at its top-most and bottom-most portions to form a singular closed loop (as in FIG. 5) and, instead of the secondary flex interconnect 214 being coupled to the primary flex interconnect on its inner most face (the face farthest from housing 406), the secondary flex interconnect 214 of FIG. 5 is connected to the primary flex interconnect on its outer most outward facing face (that is, the face closest to the housing 406).

Turning to FIG. 6, another alternative cross-sectional, side view of an ultrasound probe 600, in accordance with aspects of the present disclosure is depicted. Ultrasound probe 600 contains the same components, with the addition of a central heat sink 602, arranged in a slightly different geometric configuration, than those depicted in ultrasound probe 500. Components and/or features and/or configurations already described above with reference to FIGS. 2-5, therefore continue to be numbered identically and are not reintroduced below.

Looking at FIG. 6, the ultrasound probe 600 maintains the same geometric configuration of components as those shown in FIG. 5, with the exception of ASIC heat sinks 207, secondary flex interconnect 214, and central heat sink 602. In the embodiment shown in FIG. 6, the ASIC heat sinks 207 may be coupled to the primary flex interconnect 212 on a face opposite to that coupled to the ASICs 202, so that heat produced by ASICs 202 may be transferred across primary flex interconnect 212 directly to ASIC heat sinks 207. On a face of ASIC heat sink 207 opposite to that coupled to primary flex interconnect 212, ASIC heat sink 207 may be coupled to central heat sink 602. Central heat sink 602 may be arranged along centerline 410 and be secured in ultrasound probe 600 by coupling on opposite lateral faces (according to elevation axis 220) to ASIC heat sinks 207, as described above. In alternative embodiments, central heat sink 602 may be secured in an ultrasound probe by one or more attachments/couplings to ASIC heat sink(s) 207, housing 406 and/or an active cooling heat exchanger. It will be appreciated that an active cooling heat exchanger may reside entirely within the probe, entirely external to the probe, or be partially integrated into the probe, and that the active cooling heat exchanger may serve to transfer heat from central heat sink 602 over probe cable 408. As is shown in FIG. 6, primary flex interconnect 212 is in the same geometric configuration as shown in FIG. 5; however, instead of primary flex interconnect 212 being coupled to a secondary flex interconnect 214 in a closed loop configuration (as seen in FIG. 5), primary flex interconnect 212 is instead coupled on its first side 224 to a first strip of secondary flex interconnect 214 and on its second side 226 to a second strip of secondary flex interconnect 214. Each of the two secondary flex interconnects 214 is coupled to a corresponding circuit board 216, with the two circuit boards 216 coupled to the most lateral (according to elevation axis 220) faces of the two secondary flex interconnects 214, such that each circuit board 216 is coupled to the face of the secondary flex interconnect 214 that is closest to housing 406.

As shown in FIGS. 2-6, the transducer array includes a single acoustic module (acoustic stack 204) and more than one electric modules (ASICs 202), where each of the electric modules is in electronic communication with the single acoustic module via the primary flex interconnect 212. As shown in FIGS. 4-6, each probe contains only a single transducer array including the single acoustic module and one or more electric modules. This configuration allows for a simplified probe design that is easier to manufacture. In some embodiments, a probe may include multiple transducer arrays aligned with one another along the elevation direction 220. Thus, the probes shown in FIGS. 4-6 may be referred to as having only one transducer module array containing a single acoustic module and one or more electric modules physically decoupled from but in electrical communication with the acoustic module. Further, the single transducer module array may include only one base unit (e.g., acoustic backing and acoustic heat sink) and primary flex interconnect.

Having addressed the geometric differences between FIGS. 4, 5 and 6, it may now be apparent how the various components of an ultrasound probe comprising a transducer array (such as transducer arrays 200 and/or 300 from FIGS. 2 and 3), plus non-transducer array components (such as lens 404, housing 406, coaxial probe cable 402, probe cable assembly 408, and central heat sink 602) may be rearranged to suit the desired outcome for probe shape during manufacturing.

FIGS. 2-6 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

A technical effect of the disclosure is the generation of an ultrasound probe that decouples the acoustic module (e.g., acoustic stack) and electric modules (e.g., ASICs) from one another, leading to a high integration level without thermal coupling between modules. Another technical effect owing to such a decoupling is the generation of a curved transducer array without damage to the electric modules. For example, since the acoustic module and one or more electric modules are spaced apart from one another, the acoustic module may be curved to accommodate a curved transducer array face while the one or more electric modules may remain flat and uncurved, thereby preserving their electrical function. Yet another technical effect due to such a decoupling is the freedom to use different pitches (e.g., geometries, such as length or width) for the electric modules and acoustic module.

In one embodiment, an ultrasound transducer array for an ultrasound probe, comprises an acoustic backing, a flex interconnect (such as, a primary flex interconnect) coupled to the backing at a first surface of the flex interconnect, a matrix acoustic array (such as, an acoustic stack) coupled to a second surface of the flex interconnect, the second surface opposite the first surface, and an electric module coupled to the second surface of the flex interconnect at a location spaced away from where the matrix acoustic array is couple to the flex interconnect. In another embodiment, the ultrasound transducer array is an only module array of the probe and wherein the acoustic backing is a single acoustic backing and the flex interconnect is a single flex interconnect of the ultrasound transducer array. In yet another embodiment, the ultrasound transducer array may include a flex interconnect, including a top side connected between a first side and second side of the flex interconnect.

In one example, the ultrasound transducer may be arranged such that each of the first side and second side are arranged parallel to one another and perpendicular to the top side. In another example, the ultrasound transducer array may be geometrically arranged such that the electric module is coupled to one of the first side and the second side and the matrix acoustic array is coupled to the top side. In yet another example, the ultrasound transducer array may be arranged such that the matrix acoustic array is planar and coupled to the second surface of the top side of the flex interconnect.

In another embodiment, the ultrasound transducer array may be arranged such that each of the first side and second side are arranged parallel to one another and perpendicular to a plane arranged normal to the top side, wherein the matrix acoustic array is curved and coupled to the second surface of the top side of the flex interconnect, wherein the top side of the flex interconnect is curved along with the curved matrix acoustic array, and wherein the first side and second side of the flex interconnect are planar. Furthermore, in another embodiment, the ultrasound transducer array may be arranged such that the electric module comprises two or more ASICs coupled along the first side or second side of the flex interconnect and spaced apart from one another along the flex interconnect. In yet another embodiment, the ultrasound transducer array may be arranged such that the acoustic backing is coupled to only the top side of the flex interconnect and further comprising a first heat sink coupled directly to the acoustic backing. The ultrasound transducer may further comprise two or more second heat sinks coupled to the second surface of the flex interconnect, each of the two or more second heat sinks positioned opposite to and adjacent each of the two or more ASICs, where the first heat sink is separated from each of the two or more second heat sinks.

In one example, the ultrasound transducer may further comprise a circuit board and a secondary flex interconnect coupled to the flex interconnect and the circuit board. Continuing this example, the ultrasound transducer may also further comprise a coaxial probe cable electrically coupled to the circuit board. In another example, the ultrasound transducer array may be arranged such that matrix acoustic array has a first pitch and the electric module has a second pitch, the first pitch different than the second pitch. In yet another example, the electric module may be directly coupled to the second surface of the flex interconnect in the ultrasound transducer array.

Moreover, in one embodiment, the ultrasound transducer array may be arranged such that the electric module is coupled to the second surface of the flex interconnect through a chip packaging. In another embodiment, the ultrasound transducer may further comprise an interposer flex positioned between the matrix acoustic array and the second surface of the flex interconnect, where the interposer flex electrically couples the matrix acoustic array to the flex interconnect.

In one embodiment, an ultrasound transducer array for an ultrasound probe comprises a single base unit comprising an acoustic backing and heat sink, a single primary flex interconnect coupled to the acoustic backing and electrically coupled to a circuit board, at least two ASICs individually coupled to a first surface of the flex interconnect, and a single matrix acoustic array disposed on the first surface of the flex interconnect and spaced away from the one or more ASICs, the matrix acoustic array comprising a plurality of acoustic stack elements. In another embodiment, the primary flex interconnect comprises a first side parallel to a second side and perpendicular to a top side, and curved portions between the first side and top side and between the top side and second side. In yet another embodiment, the ultrasound transducer array may be arranged such that each ASIC of the at least two ASICs is coupled to one of the first side and second side of the primary flex interconnect and wherein the matrix acoustic array is coupled to the top side of the primary flex interconnect through an interposer flex that electrically couples the matrix acoustic array to the primary flex interconnect.

In one example, the ultrasound transducer array may be arranged such that the circuit board includes two circuit boards and the primary flex interconnect is electrically coupled to the two circuit boards through two secondary flex interconnects, where a first end of each of the two secondary flex interconnects is coupled to one of the first side and second side of the primary flex interconnect and a second end of each of the two secondary flex interconnects is coupled to one of the two circuit boards and further comprising a coaxial probe cable coupled to each of the two circuit boards. In another example, the ultrasound transducer array may be arranged such that the circuit board includes two circuit boards and wherein the primary flex interconnect is electrically coupled to the two circuit boards through a single secondary flex interconnect, where a first end of the secondary flex interconnect is coupled to each of the first side and second side of the primary flex interconnect and a second end of the secondary flex interconnect is coupled to each of the two circuit boards and further comprising a coaxial probe cable coupled to each of the two circuit boards. In yet another example, an ultrasound transducer probe having a single module, may comprise a single base unit comprising an acoustic backing and heat sink, a single primary flex interconnect coupled to the acoustic backing, at least two ASICs individually coupled to a first surface of the flex interconnect, a single matrix acoustic array disposed on the first surface of the flex interconnect and spaced away from the one or more ASICs, the matrix acoustic array comprising a plurality of acoustic stack elements, a circuit board, and a coaxial probe cable.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound transducer array for an ultrasound probe, comprising:
   a single base unit comprising an acoustic backing and a heat sink;
   a single primary flex interconnect coupled to the acoustic backing and electrically coupled to a circuit board;
   at least two application specific integrated circuits (ASICs) individually coupled to a first surface of the primary flex interconnect; and
   a single matrix acoustic array disposed on the first surface of the primary flex interconnect and spaced away from the at least two ASICs, the matrix acoustic array comprising a plurality of acoustic stack elements, a location where the at least two ASICs couple to the first surface being in a different plane of the primary flex interconnect than where the matrix acoustic array couples to the primary flex interconnect,
      where the acoustic backing is directly coupled to a second surface of the primary flex interconnect, the second surface arranged opposite the first surface of the primary flex interconnect,
      where the acoustic backing is arranged directly beneath, relative to a vertical axis of the ultrasound transducer array, the matrix acoustic array, and
      where a top side of the primary flex interconnect is positioned between the acoustic backing and the matrix acoustic array in a direction along the vertical axis of the ultrasound transducer array, and wherein the acoustic backing and the matrix acoustic array are both positioned between a first side of the primary flex interconnect and a second side of the primary flex interconnect, wherein two or more ASICs of the at least two ASICs are coupled along the first side or the second side of the primary flex interconnect, wherein one ASIC heat sink is thermally coupled to each of the two or more ASICs coupled along the first side or the second side of the primary flex interconnect, and wherein the circuit board includes two circuit boards, and wherein the primary flex interconnect is electrically coupled to the two circuit boards through two secondary flex interconnects, where a first end of each of the two secondary flex interconnects is coupled to one of the first side and the second side of the primary flex interconnect and a second end of each of the two secondary flex interconnects is coupled to one of the two circuit boards, and further comprising a coaxial probe cable coupled to each of the two circuit boards.

2. The ultrasound transducer of claim 1, further comprising an interposer flex positioned between the matrix acoustic array and the second surface of the primary flex interconnect, where the interposer flex is configured to electrically couple the matrix acoustic array to the primary flex interconnect.

3. The ultrasound transducer array of claim 1, wherein the primary flex interconnect comprises the first side parallel to the second side and perpendicular to the top side of the primary flex interconnect, and curved portions between the first side and the top side of the primary flex interconnect and between the top side and the second side of the primary flex interconnect.

4. The ultrasound transducer of claim 3, wherein each ASIC is coupled to the primary flex interconnect through an interposer flex that is configured to electrically couple the matrix acoustic array to the primary flex interconnect.

5. An ultrasound transducer probe having a single transducer array, comprising:
 a single base unit comprising an acoustic backing and an acoustic heat sink coupled to the acoustic backing;
 a single primary flex interconnect coupled to the acoustic backing at a first surface of the primary flex interconnect;
 a plurality of ASICs individually coupled to a second surface of the primary flex interconnect, the second surface arranged opposite to the first surface of the primary flex interconnect;
 a single matrix acoustic array disposed on the second surface of the primary flex interconnect and spaced away from the plurality of ASICs, the matrix acoustic array coupled to a different plane of the primary flex interconnect than the plurality of ASICs, the matrix acoustic array comprising a plurality of acoustic stack elements, the acoustic backing arranged directly beneath, relative to a vertical axis of the ultrasound transducer probe, the matrix acoustic array,
  where a top side of the primary flex interconnect is positioned between the acoustic backing and the matrix acoustic array in a direction along the vertical axis of the ultrasound transducer probe, and
  where the acoustic backing and the matrix acoustic array are both positioned between a first side of the primary flex interconnect and a second side of the primary flex interconnect;
 a secondary flex interconnect coupled to the primary flex interconnect and at least two circuit boards; and
 a coaxial probe cable coupled to the at least two circuit boards,
 wherein two or more ASICs of the plurality of ASICs are coupled along the first side or the second side of the primary flex interconnect, and
 wherein one ASIC heat sink is thermally coupled to each of the two or more ASICs coupled along the first side or the second side of the primary flex interconnect.

6. The ultrasound transducer array of claim 5, wherein the top side of the primary flex interconnect is defined by a first plane of the multiple planes and the first side and the second side of the primary flex interconnect are defined by a second plane of the multiple planes.

7. The ultrasound transducer array of claim 6, wherein each of the first side and the second side of the primary flex interconnect is arranged parallel to one another and perpendicular to the top side of the primary flex interconnect.

8. The ultrasound transducer array of claim 7, wherein the matrix acoustic array is coupled to the top side of the primary flex interconnect.

9. The ultrasound transducer array of claim 7, wherein the matrix acoustic array is planar.

10. The ultrasound transducer array of claim 6, wherein each of the first side and the second side of the primary flex interconnect are arranged parallel to one another and perpendicular to a plane arranged normal to the top side of the primary flex interconnect, wherein the matrix acoustic array is curved and coupled to the second surface of the top side of the primary flex interconnect, wherein the top side of the primary flex interconnect is curved along with the curved matrix acoustic array, and wherein the first side and the second side of the primary flex interconnect are planar.

* * * * *